United States Patent [19]

Boussignac et al.

[11] Patent Number: 5,538,002
[45] Date of Patent: Jul. 23, 1996

[54] DEVICE FOR RESPIRATORY ASSISTANCE

[76] Inventors: Georges Boussignac, 1, Avenue do Provence, 92160 Antony, France; Jean-Claude Labrune, 2 Avenue de Guyenne, 92160 Antony, France

[21] Appl. No.: 326,256

[22] Filed: Oct. 20, 1994

[30] Foreign Application Priority Data

Sep. 14, 1994 [FR] France .................................. 94 11062

[51] Int. Cl.⁶ .................................................. A61M 16/04
[52] U.S. Cl. ............................. 128/207.16; 128/207.14; 128/207.15; 128/911; 128/912
[58] Field of Search ........................ 128/200.26, 204.23, 128/205.23, 207.14, 207.15, 207.16, 207.17, 911, 912, 204.22, 204.21, 203.12, 203.25, 205.25

[56] References Cited

U.S. PATENT DOCUMENTS

| | | | |
|---|---|---|---|
| 2,791,217 | 5/1957 | Iskauder | 128/203 |
| 3,173,418 | 3/1965 | Baran | 128/351 |
| 3,211,152 | 10/1965 | Stern | 128/351 |
| 3,437,747 | 4/1969 | Sheldon | 178/6 |
| 3,504,676 | 4/1970 | Lomholt | 128/207.15 |
| 3,707,151 | 12/1972 | Jackson | 128/351 |

(List continued on next page.)

FOREIGN PATENT DOCUMENTS

| | | |
|---|---|---|
| 898753 | 5/1984 | Belgium . |
| 0042321 | 12/1981 | European Pat. Off. . |
| 0074809 | 3/1983 | European Pat. Off. . |
| 0112668 | 7/1984 | European Pat. Off. . |
| 0152694 | 8/1985 | European Pat. Off. . |
| 0153991 | 9/1985 | European Pat. Off. . |
| 0245142 | 11/1987 | European Pat. Off. . |
| 0390684 | 10/1990 | European Pat. Off. . |
| 2613639 | 10/1900 | France . |
| 160709 | 6/1903 | Germany . |
| 2353153 | 4/1975 | Germany . |
| 1171439 | 11/1969 | United Kingdom . |
| 2057273 | 4/1981 | United Kingdom . |
| WO84/01513 | 3/1984 | WIPO . |
| WO85/02101 | 4/1985 | WIPO . |
| WO88/00071 | 1/1988 | WIPO . |
| WO89/06983 | 4/1989 | WIPO . |
| WO90/11792 | 5/1990 | WIPO . |
| WO93/21982 | 5/1993 | WIPO . |

OTHER PUBLICATIONS

Beydon, L. et a., "Mechanical Ventilation Without A Ventilator: Utilisation of the Properties of a New Intubation Tube", INSERM U.296, DAR 11, Hospital Henri Mondor, F–94010 Cretail, France, Absract.

Boussignac, G. et al., "Efficiency of an Endotracheal New Set Up Allowing A Continuous Additional Gas Flow", Departement D'Anesthesie–Reanimation, Hospital H. Mondor, 94010 Creteil, 13 pages.

Brochard, L. et al., "Constant Flow Insufflation Prevents Arterial Oxygen Desaturation During Off–Ventilator Disconnection", Reanimation Medicale, Service d'Anesthesie–Reanimation (DARl) etINSERM U. 296, Hospital Henri Mondor, 94010 Cretail, France 25 pages.

(List continued on next page.)

*Primary Examiner*—Edgar S. Burr
*Assistant Examiner*—William J. Deane, Jr.
*Attorney, Agent, or Firm*—Fisher, Christen & Sabol

[57] ABSTRACT

Device for respiratory assistance, comprising a tube (4) which forms a main channel (5) and which is intended to be connected via its distal end (3) to the respiratory tract of a patient so that said main channel (5) connects the respiratory system of said patient to the outside, with said device moreover comprising at least one auxiliary channel (8) formed in the wall of said tube (4) and permitting the insufflation of a respirable gaseous jet into said respiratory system and opening into said main channel (5) in the vicinity of the distal end (7) of the latter.

According to the invention, this device is distinguished by the fact that it comprises a controlled valve (21) capable of closing at least partially the proximal end of said main channel (5), at least during insufflation of said gaseous jet.

12 Claims, 5 Drawing Sheets

U.S. PATENT DOCUMENTS

| | | | |
|---|---|---|---|
| 3,717,174 | 2/1973 | Dewall | 137/565 |
| 3,821,510 | 6/1974 | Muncheryan | 219/121 |
| 3,821,570 | 6/1974 | Burson | 310/70 |
| 3,859,995 | 1/1975 | Colston | |
| 3,881,479 | 5/1975 | Carden | 128/145.8 |
| 3,915,173 | 10/1975 | Brekke | 128/351 |
| 3,982,541 | 9/1976 | L'Esperance, Jr. | 128/303.1 |
| 3,991,764 | 11/1976 | Incropera et al. | 218/303.1 |
| 4,176,662 | 12/1979 | Frazer | 128/6 |
| 4,183,102 | 1/1980 | Guiset | 3/1.4 |
| 4,265,237 | 5/1981 | Schwanbom et al. | 128/204.24 |
| 4,270,530 | 6/1981 | Baum et al. | 128/204.25 |
| 4,289,128 | 9/1981 | Rusch | 128/207.15 |
| 4,299,237 | 11/1981 | Foti | 128/742 |
| 4,418,688 | 12/1983 | Loeb | 128/6 |
| 4,423,725 | 1/1984 | Baran et al. | 128/207.15 |
| 4,470,407 | 9/1984 | Hussein | 128/6 |
| 4,471,775 | 9/1984 | Clair et al. | 128/205.24 |
| 4,520,812 | 6/1985 | Freitag et al. | 128/204.25 |
| 4,526,196 | 7/1985 | Pistillo | 128/207.15 |
| 4,552,142 | 11/1985 | Hoffman et al. | 128/207.16 |
| 4,573,462 | 3/1986 | Baum | 128/204.25 |
| 4,581,017 | 4/1986 | Sahota | 604/101 |
| 4,584,998 | 4/1986 | McGrail | 128/604 |
| 4,592,353 | 6/1986 | Daikuzono | 128/303.1 |
| 4,612,929 | 9/1986 | Schubert et al. | 128/204.25 |
| 4,649,914 | 3/1987 | Kowalewski | 128/207.15 |
| 4,657,014 | 4/1987 | Edelman et al. | 128/303.1 |
| 4,694,828 | 9/1987 | Eichenbaum | 128/303.1 |
| 4,739,756 | 4/1988 | Horn | 128/207.14 |
| 4,751,924 | 6/1988 | Hammerschmidt | 128/207.15 |
| 4,762,129 | 8/1988 | Bonzel | 128/344 |
| 4,821,714 | 4/1989 | Smelser | 128/207.14 |
| 4,825,862 | 5/1989 | Sato et al. | 128/207.15 |
| 4,832,024 | 5/1989 | Boussignac et al. | 128/303.1 |
| 4,872,483 | 10/1989 | Shah | 137/557 |
| 4,976,261 | 12/1990 | Gluck et al. | 128/207.15 |
| 5,000,734 | 3/1991 | Boussignac et al. | 604/96 |
| 5,036,847 | 8/1991 | Boussignac et al. | 128/207.14 |
| 5,050,593 | 9/1991 | Poon | 128/204.23 |
| 5,161,773 | 11/1992 | Tower | 251/5 |
| 5,186,431 | 2/1993 | Tamari | 251/5 |
| 5,235,973 | 8/1993 | Levinson | 128/205.23 |
| 5,304,135 | 4/1994 | Shonk | 604/101 |
| 5,318,021 | 6/1994 | Alessi | 128/207.15 |
| 5,421,325 | 6/1995 | Cinberg et al. | 128/200.26 |

OTHER PUBLICATIONS

Brochard, L. et al., "Constant Flow Insufflation Prevents Arterial Oxygen Desaturation During Off–Ventilator Disconnection", American Thoracic Society, Abstract.

Brochard, L. et al., "Ventilatory and Hemodynamic Effects of Cario–Pulmonary Resuscitation (CPR) During Constant Flow Ventilation (CFV)", American Thoracic Society, Abstract.

Boussignac, G. et al., "Preliminary Study of a New Endotracheal Tube for Respiratory Assistance: Limitation of Hypoxia After Endotracheal Suction in Human Newborns", Neonatal Respiration, Monday P.M., p. 1150.

Isabey, et al., "Effect of Air Entranment on Airway Pressure During Endotracheal Gas Injection", 71st annual meeting of the FASEB in Washington, D.C., Mar. 29th–Apr. 2nd, 1987.

Isabey, D. et al., "Mecanisme De L'Entrainement D'Air Induit Par Des MIcrojets Gazeux, Dans Une Sonde D'Intubation", Biomecanique circulatoire et respiratoire, vol. 11, supplement au n 1(1987), pp. 80–81.

Isabey, D. et al., "Mechanical Effects Induced by Jets in Airways", Biomedical Engineering Scientific Papers, Unite de Physiologie Respiratoire INSERM (U 296), Hospital Henri Mondor, Creteil, France, Abstract.

Isabey, D. et al., "Physical Basis of Air Entrainment Induced By Microjet Gas Injection In Endotrachel Tubes", Mechanics of Breathing II: Airways, Monday P.M., p. 510.

Mion, "Preparation of Arterial Oxygen Desaturation Induced by Endotracheal Suctioning Using Constant Flow Insufflation", Abstract Presente Au Congre De l'ASA A San Francisco En Octobre Dernier (1988), p. 1.

Tranget al., "Measurement of Distal Airway Pressures in Mechanically Ventilated Infants with a New Designed Endotracheal Tube", Intensive Care Medicine 13 (6) 65, (abstract), 1987, p. 446.

Trang et al., "Limitation of Hypoxia After Tracheal Suction Using a New Designed Endotracheal Tube", Intensive Care Medicine 13 (6), 100 (abstract), 1987, p. 455.

DEVICE FOR RESPIRATORY ASSISTANCE

The present invention relates to a device for respiratory assistance which can be used on patients whose spontaneous respiration is absent or insufficient, regardless of whether or not they have been placed under artificial respiration.

Various devices are known, such as masks and oral, nasal, endotracheal or tracheotomy catheters or cannulas, which are intended to form the connection between an artificial respiration and/or anesthesia apparatus and the respiratory system of a patient. These devices, essentially in the form of tubes, can in some cases comprise immobilizing means such as tabs or flanges, in the vicinity of the proximal end, for holding them on the mouth or nose of the patient, or else inflatable balloons, in the vicinity of the distal end, for holding them by friction in the trachea.

The known devices present important disadvantages. Thus, for example, when a tube of a known type is disconnected from the artificial respirator and the patient requires oxygen-enriched air, it is necessary to introduce into said tube a catheter which is connected to an oxygen source. Furthermore, in cases of insufficient spontaneous respiration, the patient must necessarily remain connected to the respirator until spontaneous respiration has been fully re-established.

Thus, in order to remedy these disadvantages, devices for respiratory assistance have already been proposed which, in addition to the main channel formed by the tube, comprise at least one auxiliary channel, for example formed in the wall of said tube, permitting the injection of a jet of respirable gas (oxygen, air, or oxygen/air mixture) intended for ventilating the patient, this auxiliary channel opening into the main channel in the vicinity of the distal end of the latter.

However, these devices for respiratory assistance with an auxiliary channel for injection of respiratory gas present the disadvantage that said jet of respirable gas must be at a high pressure, which, on the one hand, risks traumatizing the patient's mucous membrane on which it impacts, and, on the other hand, makes it difficult, if not impossible, to humidify said respirable gas. It well known that a gaseous jet is more difficult to humidify the higher its pressure. It is important, however, that the jet of respirable gas be humidified in order to prevent the patient's mucous membranes from drying out.

The main object of the present invention is to remedy this disadvantage.

To this end, according to the invention, the device for respiratory assistance, comprising a tube which forms a main channel and which is intended to be connected via its distal end to the respiratory tract of a patient so that said main channel connects the respiratory system of said patient to the outside, with said device moreover comprising at least one auxiliary channel permitting the injection of a respirable gaseous jet into said respiratory system and opening into said main channel in the vicinity of the distal end of the latter, is distinguished by the fact that it comprises a controlled valve capable of closing at least partially the proximal end of said main channel, at least during insufflation of said gaseous jet.

Thus, due to the fact that said proximal end of the main channel is at least partially closed during insufflation of the respirable gaseous jet, the pressure of the latter can be reduced (since the escape of gas toward the surrounding atmosphere is prevented or at the very least reduced) for a similar ventilating effect. The reduction in the pressure of the ventilating gas thus makes it easy to humidify said gas, for example by bubbling or else by spraying.

Of course, said respirable gaseous jet can, in a known manner, be continuous or pulsed. If said gaseous jet is continuous, said controlled valve must, on the one hand, close the proximal end of said main channel partially or completely during the inhalation by the patient in order to obtain the reduction in pressure mentioned above, and, on the other hand, must open said proximal end partially or completely during the exhalation by said patient. The partial opening of this proximal end during the exhalation by the patient can be used as an "exhalation brake" by means of which said patient is obliged to perform beneficial respiration exercises. If, in contrast, said gaseous jet is pulsed, said controlled valve must, on the one hand, close the proximal end of said main channel partially or completely during the pulses of the gaseous jet for the same purpose of pressure reduction as before, and, on the other hand, must open said proximal end partially or completely between said pulses of the gaseous jet. Between these pulses it is of course possible to make use of the partial opening of said controlled valve to obtain an "exhalation brake".

It will be noted that it is even possible to use the device according to the invention without insufflation of respirable gas, the patient inhaling and exhaling through said channel and said controlled valve, the latter then controlling the cross section of flow of said channel.

Said controlled valve can form a single-piece assembly with said tube, or else it can be attached thereto. In this latter case, which allows standard respiratory tubes to be converted to respiratory tubes according to the present invention, it is advantageous for said controlled valve to be integral with a connection piece capable of being engaged on the proximal end of said tube.

The controlled valve can be of any known type, with electrical control, pneumatic control, etc. However, it is advantageous that in the open position it should allow the main channel to preserve an internal diameter sufficient to permit the passage, through said channel, of the instruments and medical catheters which the operator wishes to use, without interrupting the ventilation.

Thus, in a preferred embodiment, said controlled valve comprises a sealed enclosure of toroidal cross section arranged in the vicinity of the proximal end of said main channel and comprising at least one flexible and elastic inner wall which, by expanding or retracting in response to the introduction or the removal of an inflating gas into or out of said sealed enclosure, controls the cross section of flow of said main channel. It will be noted that such a valve, even when it is completely closed, permits the passage of instruments or catheters into said channel by means of forcing back said flexible inner wall.

In order to ensure that an object applied inadvertently against the proximal orifice of said tube does not occlude said main channel and prevent exhalation by the patient, the free edge of the proximal end of said tube comprises at least one notch.

Also for safety reasons, the device according to the present invention furthermore comprises means which receive the pressure toward the distal end of said tube and which are capable of forcing said controlled valve to open in order to free said main channel. In order further to increase safety, it is possible to provide a calibrated escape valve arranged at the proximal end of said tube, at the side opposite the free edge of the proximal end in relation to said controlled valve.

In order to increase safety still further, it is possible to arrange for the introduction and removal of the inflating gas of said sealed enclosure to result from the bidirectional displacement of a suitable volume of gas, contained in a buffer area of controllable variable volume.

Moreover, in order to prevent the jet of humidified respirable gas from striking the mucous membrane directly, with the risk of its kinetic energy traumatizing said mucous membrane, it is advantageous if, as has been described in the European Patent EP-A-0 390 684, at least the distal end of said auxiliary channel opening into the main channel is parallel thereto, and if there are provided, facing the distal orifice of said auxiliary channel, means for deflecting said jet of respirable ventilation gas toward the inside of said main channel.

Thus, the jet of humidified respirable gas passing through said auxiliary channel at low pressure is deflected toward the axis of the main channel when it penetrates into the latter. Downstream of said deflection means, that is to say inside the main channel, the pressure of said jet of respirable gas drops and the jet emerges at even lower pressure through the distal orifice of the tube. Experience has shown that downstream of the distal outlet of the tube the pressure is low and is kept constant throughout the respiratory space. This pressure is dependent on the thruput of respirable gas in the auxiliary channels. Consequently, with the device for respiratory assistance according to the invention, it is possible, for example, to supply humidified oxygen or a humidified mixture of air/oxygen directly to the lungs, at the level of the carina, and thereby to suppress the dead space which exists in current catheters and which is approximately a third of the total respiratory volume for an adult and approximately half for premature neonates.

The suppression of this dead space corresponds to an increase in performance of the respiratory cycle of over 25% in all patient cases and of almost 50% in some cases.

When the device according to the invention comprises a plurality of auxiliary channels, it is advantageous for at least some of them to be fed jointly with respirable gas. This joint feeding of said channels can be carried out by way of a distribution ring coaxial to said tube. Furthermore, said auxiliary channels which are not fed jointly can be used for the introduction of additional gaseous products, such as medicinal products.

Thus, it will be seen that the device according to the invention permits:

humidification of the insufflated respirable gas, intubation of long duration for respiratory assistance without drying, injection of medicaments or anesthetics during respiratory assistance, dynamic measurement of pressures, since it suffices to provide auxiliary channels to which suitable catheters are associated, creation of a micro flow of respirable gas in the auxiliary channels in order to prevent the obstruction of said channels by mucosal secretions, increase in the volume exchanged, since the pressure is self-limited and there is no risk of crushing of the pulmonary capillaries, decrease in the amount of oxygen in the mixture, for the same quantity of oxygen exchanged, which accordingly diminishes the side effects of the assistance, the possibility of using respirators which are less costly than the current respirators.

From the figures on the attached drawing it will be clearly understood how the invention can be realized. In these figures, identical references designate similar elements.

Figure 1:
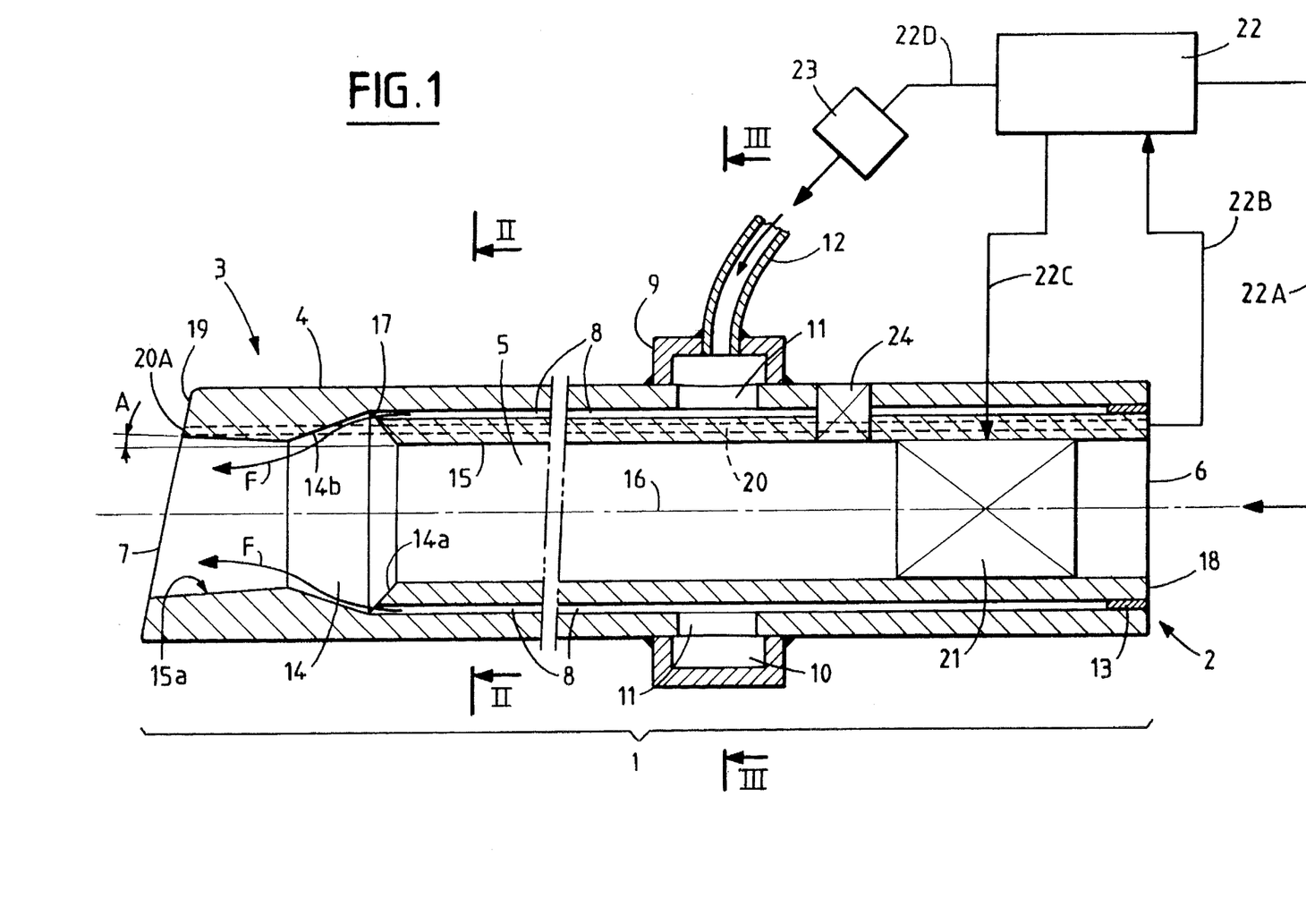
FIG. 1 is a diagrammatic and partial view, in enlarged axial section, of one embodiment of the device of the invention.

FIG. 1 represents, diagrammatically and on a large scale, the proximal 2 and distal 3 ends of a single-piece embodiment I of the device according to the invention. This single-piece embodiment can constitute, for example, an oronasal endotracheal catheter with or without balloon, a pediatric endotracheal catheter, a gas-monitoring catheter, an endobronchial catheter, a nasopharyngeal catheter, an anatomical intubation catheter for infants, a Cole neonatal catheter, a Gedel cannula catheter, a nasal oxygen therapy catheter, a nasal or bucconasal mask or a nasal balloon for treatment of sleep apnea.

The device I comprises a tube 4, flexible or preformed (to adapt to the morphology of the patient), delimiting a main channel 5 open, via the orifice 6, at the proximal end 2, and, via the orifice 7, at the distal end 3.

Thus, the main channel 5 is capable of ensuring a passage between the orifices 6 and 7, of which one (the orifice 7) is intended to be positioned inside the airways of a patient, and of which the other (the orifice 6) is intended to be positioned to the outside of said patient. This orifice 6 can be open to the surrounding air, and in this case the patient can inhale fresh air and exhale vitiated air through the main channel 5. It is also possible, as is explained hereinafter, to connect the orifice 6 to a source of pressurized respirable gas and to provide a system of unidirectional valves so that the patient inhales the respirable gas from said source through said main channel 5 and exhales the vitiated gas to the surrounding air, likewise through this main channel.

The diameter of the main channel 5 is of the order of a few millimeters. Satisfactory tests have been carried out using diameters of 3 mm, 7 mm, 8 mm and 12 mm.

In addition, auxiliary channels 8 are formed within the thickness of the wall of the tube 4, said auxiliary channels 8 extending over almost the whole length of the main channel 5. These auxiliary channels 8 are intended to be connected to a source of pressurized respirable gas. This pressure is, for example, at most equal to 0.5 bar, and it is adjustable.

Figure 3:
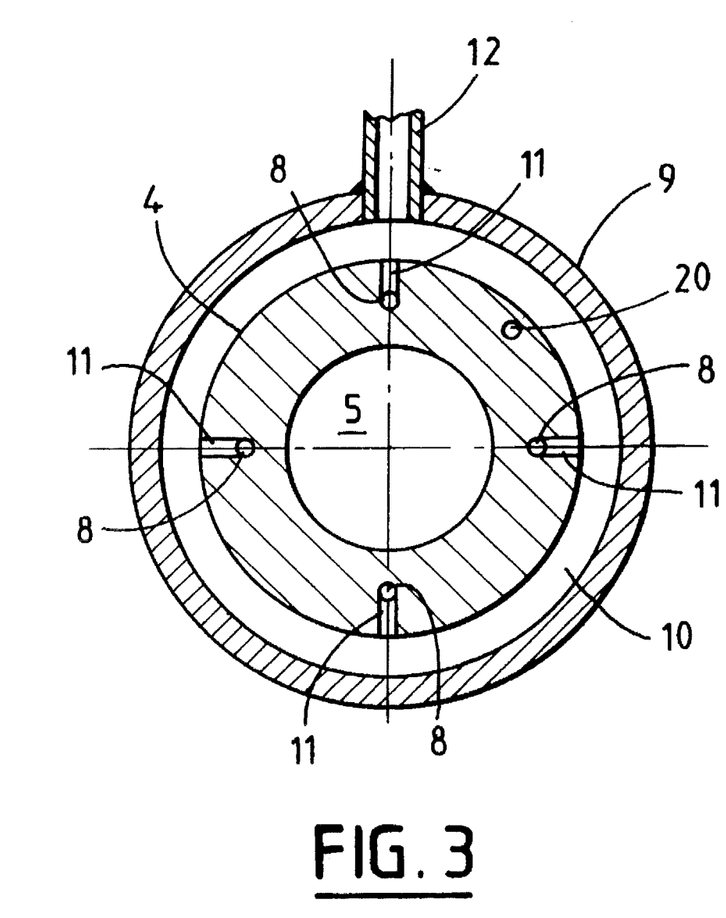

As is represented in FIGS. 1 and 3, the connection to the source of pressurized respirable gas can be obtained by means of a ring 9 which surrounds the tube 4 sealingly toward the proximal end 2 and delimits a sealed annular chamber 10 around said tube. The auxiliary channels 8 are brought into communication with the chamber 10 by means of local tears 11 in the wall of the tube 4, and said chamber 10 is connected to said source of respirable gas via a conduit 12. The proximal ends of the channels 8 are of course closed off, for example by plugs 13 which are introduced from the proximal end face 18 of the tube 4.

The auxiliary channels 8 have a diameter smaller than that of the main channel 5. The diameter of the auxiliary channels 8 is preferably less than 1 mm, and it is advantageously of the order of 400 to 800 microns. Toward the distal end, the auxiliary channels 8 open out into a recess 14 of the inner wall 15 of the tube 4. The recess 14 is annular and centered on the axis 16 of the distal end 3. It comprises a face 14a which is substantially transverse or slightly inclined, in such a way as to constitute a widening of the main channel 5, and into which said auxiliary channels 8 open via their orifices 17, as well as a face 14b following the face 14a and converging in the direction of the axis 16.

Between the converging inclined face 14b and the distal orifice 7, the inner wall 15 preferably has a part 15a widening slightly toward the outside, as is illustrated by the angle A in FIG. 1.

Thus, when the auxiliary channels 8 are fed with pressurized respirable gas by way of the elements 9 to 12, the corresponding gaseous jets strike the inclined face 14b, which deflects them in the direction of the axis 16 (arrows F in FIG. 1), generating in the vicinity of said axis a zone of low pressure promoting the gas circulation inside the main channel 5, from the proximal orifice toward the distal orifice. The inhalation by the patient is thus promoted.

The distance between each of the orifices 17 and the orifice 7 is preferably of the order of 1 to 2 cm.

At least one supplementary channel 20 is provided within the thickness of the tube 4 so as to open out at 20A in the vicinity of the distal end 19 of the tube 4 and to serve as a pressure tap.

The device 1 moreover comprises a controlled valve 21 capable of closing off at least partially the proximal end 2 of the main channel 5 during the insufflation of said gaseous jet, as well as a supply and control device 22. This latter device 22 is connected:

to the proximal end 2 of the tube 4 via a connection 22A, to the supplementary channel 20 via a connection 22B, to the controlled valve 21 via a connection 22C, and to the conduit 12 via a connection 22D in which a humidifier 23 is inserted.

The modes of functioning of the device according to the invention are as follows:

in the artificial respiration mode, the device 22 cuts out the connection 22D, orders the at least partial opening of the valve 21 via the connection 22C, and delivers respirable gas into the tube 4 by way of the connection 22A;

in the respiratory assistance mode, the device 22 cuts out the connection 22A in order to bring the orifice 6 into communication with the atmosphere, orders the alternate opening and closure of the valve 21 via the connection 22C, and delivers a continuous or pulsed jet of respirable gas to the auxiliary channels 8 via the connection 22D, through the humidifier 23. In this respiratory assistance mode, the valve 21 is closed, partially or completely, during the insufflation of respirable gas into the patient through the channels 8, and at least partially open during the exhalation by said patient through the tube 4 toward the outside. On account of the fact that the proximal end 2 of the tube 4 is closed off during the insufflation of respirable gas, the pressure of the latter can be low, which fact allows it to be humidified easily in the humidifier 23.

In the two modes of functioning, the supply and control device 22 is informed of the pressure prevailing in the lungs of the patient by way of the connection 22B. In the case of an abnormal excess pressure, the device 22 can thus trigger an alarm and stop the insufflation of respirable gas through the connection 22A or the connection 22D.

In order further to increase safety, a calibrated escape valve 24 can be provided in the proximal end 2 of the tube 4, at the side opposite the orifice 6 in relation to the controlled valve 21. Thus, in the event of accidental excess pressure, an escape of gas is established outside the patient, through the wall of the tube 4, in order instantly to eliminate this excess pressure.

Figure 4:
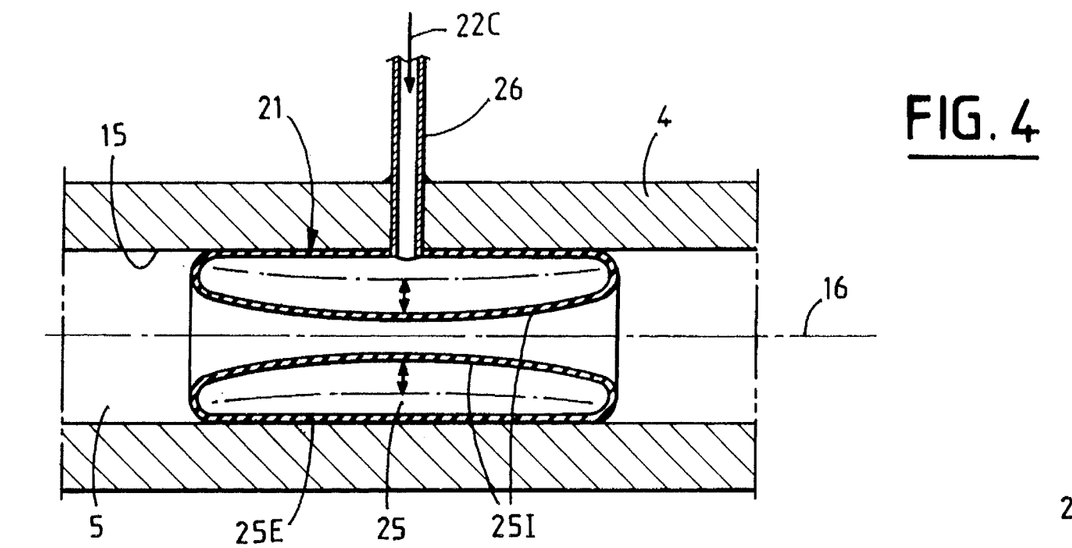
FIG. 4 illustrates diagrammatically, in enlarged axial section, a preferred embodiment for the valve arranged at the proximal end of the device according to the invention.

A preferred embodiment for said controlled valve 21 has been illustrated diagrammatically in FIG. 4. In this embodiment, the controlled valve 21 comprises an elastic inflatable bladder 25 of toroidal cross section, the outer wall 25E of which bears against the inner wall 15 of the main channel 5 and which is linked to the connection 22C via a conduit 26. Thus, inflating gas delivered to said bladder 25 by the device 22 allows the inner wall 25I thereof to move closer together, in such a way as to restrict or close off the main channel, whereas said bladder retracts spontaneously under the action of its inherent elasticity when said inflating gas is evacuated from the bladder, thereby freeing said main channel (in FIG. 4 the bladder 25 is represented in a position halfway between opening and closure).

When this valve 21 is in the open position, the inner wall 25I of the bladder 25 is spaced apart and creates sufficient space for medical and surgical apparatus to be passed through the tube 4. It will be noted that even in the closed position such medical and surgical apparatus can be passed by force through the valve 21 by virtue of the elasticity of the inner wall 25I.

Figure 5:
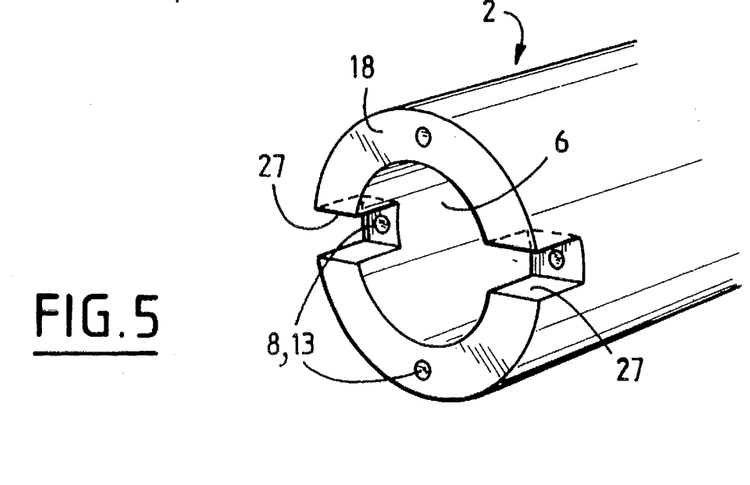
FIG. 5 shows, in diagrammatic and partial perspective, the proximal end of the device according to the invention.

As is shown in FIG. 5, the proximal annular face 18 delimiting the proximal orifice 6 of the tube 4 is provided with notches 27 which permit communication between the main channel 5 and the outside even if the orifice 6 is blocked by an object bearing accidentally thereon.

From the above text it will therefore be seen that, by virtue of the invention, a humidified respiratory assistance is achieved which is not aggressive in respect of the patient, with almost total disappearance of the dead space inherent to the known tubes.

The tube 4 can comprise, at the distal end 3, an inflatable balloon (not shown) equipped with the necessary safety devices, or any other balloon capable of acting as a safety valve in the event of overpressure in the lungs. This optional balloon can be inflated from a supplementary channel (not shown) associated with the tube 4.

In addition, at least one of the auxiliary channels 8 can be specially designed for delivering a medical fluid.

Figure 2:
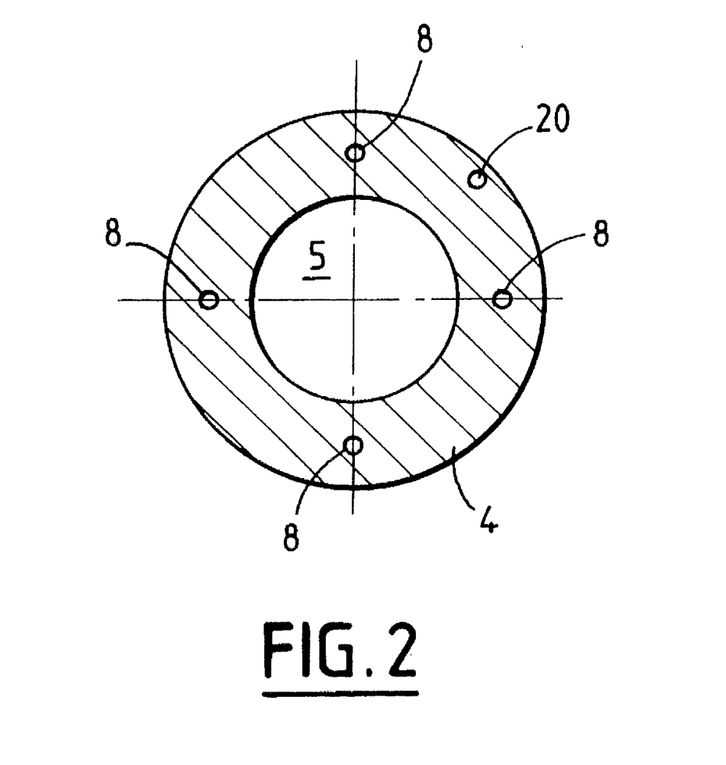
FIGS. 2 and 3 are cross sections along the lines II—II and III—III, respectively, in FIG. 1.

As is shown in FIGS. 2 and 3, the auxiliary channels 8 are arranged uniformly about the axis of the tube 4. They vary in number depending on the applications (adult or child), but they are generally between three and nine in number.

The tube 4 of the device according to the invention can be made of any material already used in respiration catheters, for example of a polyvinyl chloride with an optional coating of silicone or of steel permitting injections at high pressure.

The dimensions of the device according to the invention can of course vary greatly, essentially as a function of the mode of application of the tube and the size of the patient, who may be an adult, a child, an infant or a premature baby.

Figure 6:
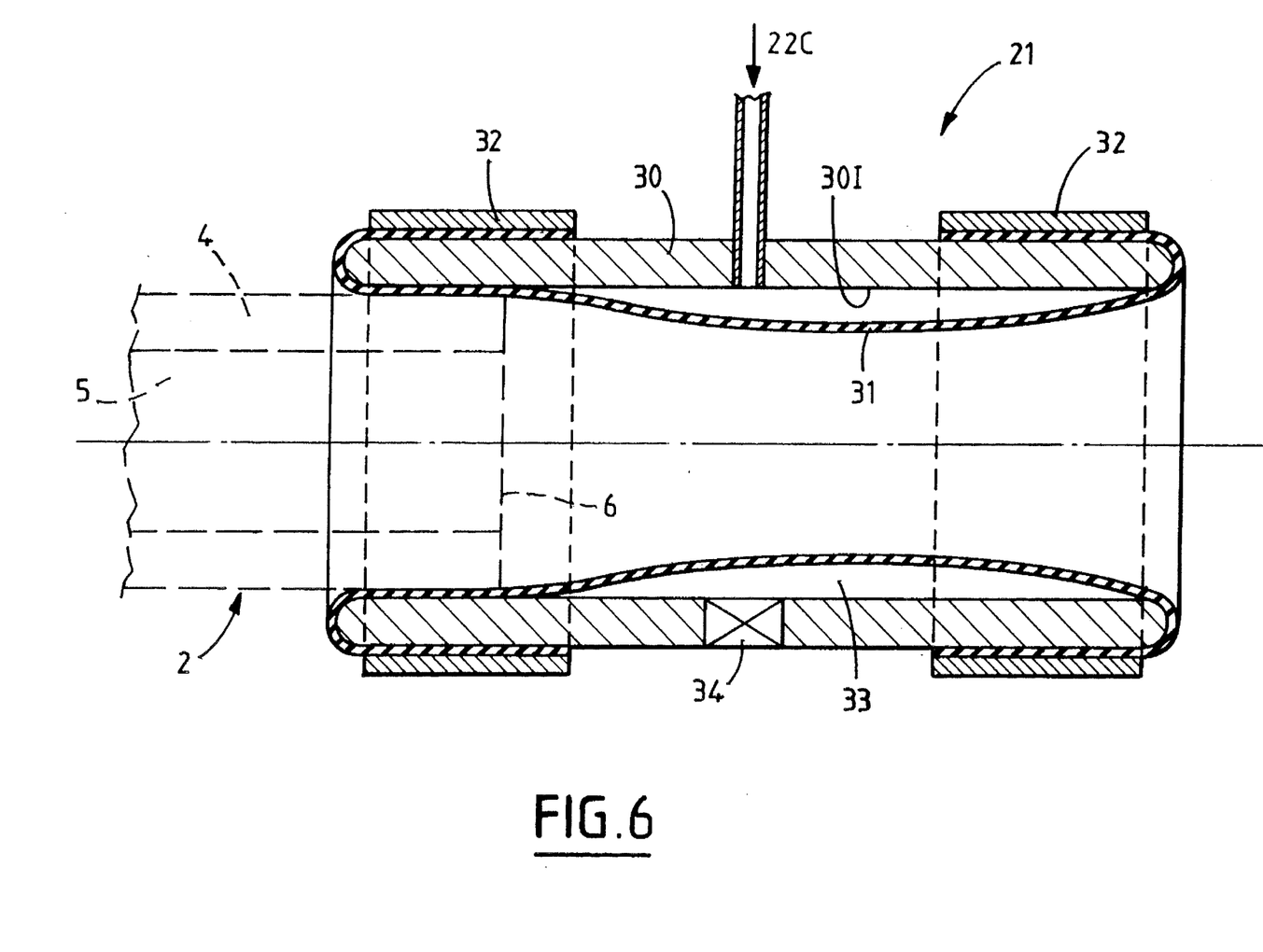
FIG. 6 illustrates diagrammatically and partially an alternative embodiment of the respiratory device according to the invention.

FIG. 6 represents an alternative embodiment permitting the use of a commercially available respiration tube 4. In this embodiment, the controlled valve 21 is integral with a rigid tubular connection piece 30 which can be engaged on the proximal end 2 of said tube. The bladder 25 in FIG. 4 has been replaced, in the example represented in FIG. 6, by a flexible and elastic tube portion 31 which is arranged inside the connection piece 30 and which is folded at its ends over the outer wall of said connection piece, where it is held by outer rings 32. The inflation conduit 22C opens into the cavity 33 formed between the inner wall 30I of the connection piece 30 and said flexible and elastic tube portion 31. It will be readily understood that the valve in FIG. 6 functions in an identical manner to that in FIG. 4. A calibrated escape valve 34 is provided for bringing the cavity 33 and the outside atmosphere into communication, if necessary.

Figure 7A:
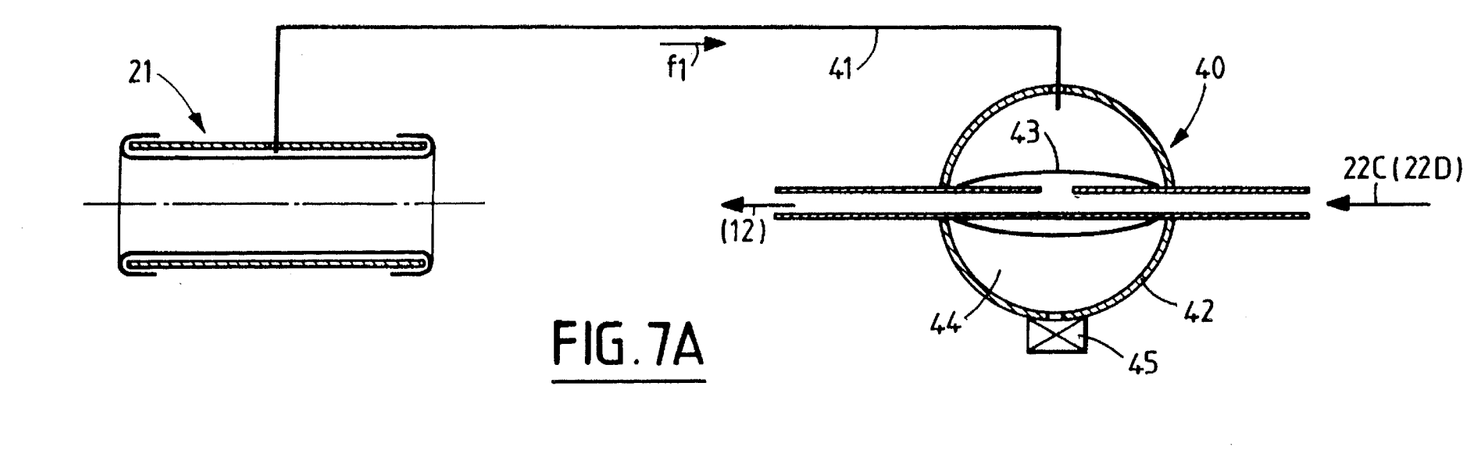
FIGS. 7A and 7B illustrate diagrammatically a device for controlling the closure and opening of the valves in FIGS. 4 and 6.
Figure 7B:
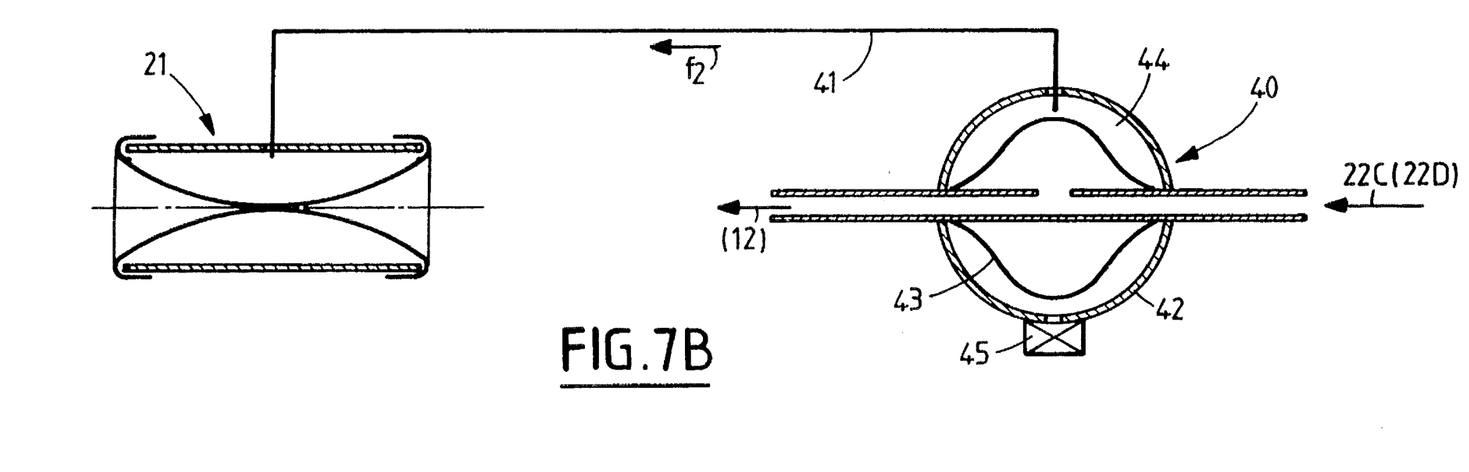

The safety inflation device of the controlled valve 21 (FIG. 4 or FIG. 6), shown diagrammatically by FIGS. 7A and 7B, comprises a buffer area 40 which is connected to the bladder 25 or to the cavity 33 by way of a communication 41.

The buffer area 40 consists, for example, of a rigid outer envelope 42 and an inflatable inner envelope 43 which delimit between them a space 44 of variable volume. It is this space 44 of variable volume which is connected to the bladder 25 or to the cavity 33 by way of the communication 41. Moreover, the inflatable elastic inner envelope 43 is connected to the device 22. As is represented in FIGS. 7A and 7B, the controlled valve 21 can be connected to said device 22 via the connection 22C (as described above) or via the connection 22D (alternative).

A calibrated escape valve 45 is provided on the outer envelope 42 in order to prevent any overpressure in the space 44 of variable volume.

Thus, the introduction and removal of the gas for inflating said controlled valve 21 results from the bidirectional displacement, within the communication 41, of the gas contained in the space 44 of variable volume. For example, the space 44, when the inner envelope 43 is deflated, has a volume equal to the inner volume of the bladder 25 or of the cavity 33 when the valve 21 is completely closed.

When no inflating gas is delivered to the buffer area 40 (FIG. 7A), the inner envelope 43 is deflated and the elasticity of the bladder 25 or of the wall 31 of the valve 21 drives the gas contained therein (see the arrow f1) into the space 44 of variable volume by way of the communication 41. The valve 21 is then in the open position.

In contrast, when inflating gas arrives in the inner envelope 43, the latter inflates and drives the gas from the space 44 toward the bladder 25 or the cavity 33 by way of the communication 41 (see the arrow f2).

We claim:

1. A device for respiratory assistance, comprising:
   (a) a tube (4) which forms a main channel (5) and which is intended to be connected via its distal end (3) to the respiratory tract of a patient so that said main channel (5) connects the respiratory system of said patient to the outside;
   (b) at least one auxiliary channel (8) permitting the insufflation of a respirable gaseous jet into said respiratory system and opening into said main channel (5) in the vicinity of the distal end (7) of the latter;
   (c) a control valve (21) disposed in the vicinity of the proximal end of said main channel (5);
   (d) means for controlling said control valve (21) to close at least partially said proximal end of said main channel (5), at least during insufflation of said respirable gaseous jet, whereby the pressure of said respirable gaseous jet can be lowered.

2. The device as claimed in claim 1, wherein said controlled valve (21) forms a single-piece assembly with said tube (4).

3. The device as claimed in claim 1, wherein said controlled valve (21) is attached to said tube (4).

4. The device as claimed in claim 3, wherein said controlled valve (21) is integral with a connection piece (30) capable of being engaged on the proximal end (2) of said tube (4).

5. The device as claimed in claim 1, wherein said controlled valve (21) comprises a sealed enclosure (25) of toroidal cross section arranged in the vicinity of the proximal end of said main channel (5) and comprising at least one flexible and elastic inner wall (25I) which, by expanding or retracting in response to the introduction or the removal of an inflating gas into or out of said sealed enclosure, controls the cross section of flow of said main channel (5).

6. The device as claimed in claim 1, wherein the free edge (18) of the proximal end of said tube (4) comprises at least one notch (27).

7. The device as claimed in claim 1, wherein it comprises at least one pressure tap (20, 20A) arranged toward the distal end (3) of said tube (4).

8. The device as claimed in claim 7, wherein said pressure tap is formed by the orifice (20A) via which an auxiliary channel (20), formed in said wall of said tube (4), opens out in the vicinity of the distal end (19) of said tube.

9. The device as claimed in claim 7, wherein it comprises means (22) receiving the pressure taken via said pressure tap (20A) and capable of forcing said controlled valve (21) to open in order to free said main channel (5).

10. The device as claimed in claim 1, wherein it comprises a calibrated escape valve (24) arranged at the proximal end of said tube (4), at the side opposite the free edge (18) of the proximal end (2) in relation to said controlled valve (21).

11. The device as claimed in claim 5, wherein the device contains means for the bidirectional displacement of a suitable volume of gas contained in a buffer area of controllable variable volume to achieve the introduction and removal of the inflating gas of said sealed enclosure.

12. The device as claimed in claim 1, wherein at least the distal end of said auxiliary channel (8) opening into the main channel (5) is parallel thereto, and wherein there are provided, facing the distal orifice (17) of said auxiliary channel (8), means (14b) for deflecting said jet of respirable ventilation gas toward the inside of said main channel (5).

\* \* \* \* \*